US011892430B2

United States Patent
Yun et al.

(10) Patent No.: US 11,892,430 B2
(45) Date of Patent: Feb. 6, 2024

(54) VOC DETECTION PID GAS SENSOR DEVICE

(71) Applicant: TAESUNG ENVIRONMENTAL RESEARCH INSTITUTE CO., LTD., Ulsan (KR)

(72) Inventors: Gi Yeol Yun, Ulsan (KR); Seok Man Kim, Ulsan (KR); Chai Rok Lim, Ulsan (KR); Kwang Bum Park, Seongnam-si (KR); Dae Sung Lee, Yongin-si (KR)

(73) Assignee: TAESUNG ENVIRONMENTAL RESEARCH INSTITUTE CO., LTD., Ulsan (KR)

( * ) Notice: Subject to any disclaimer, the term of this patent is extended or adjusted under 35 U.S.C. 154(b) by 231 days.

(21) Appl. No.: 17/617,486

(22) PCT Filed: Dec. 10, 2020

(86) PCT No.: PCT/KR2020/018064
§ 371 (c)(1),
(2) Date: Dec. 8, 2021

(87) PCT Pub. No.: WO2021/157838
PCT Pub. Date: Aug. 12, 2021

(65) Prior Publication Data
US 2022/0236223 A1    Jul. 28, 2022

(30) Foreign Application Priority Data
Feb. 5, 2020 (KR) .................. 10-2020-0013925

(51) Int. Cl.
*G01N 27/64* (2006.01)
*G01N 33/00* (2006.01)

(52) U.S. Cl.
CPC ......... *G01N 27/64* (2013.01); *G01N 33/0047* (2013.01); *G01N 33/0009* (2013.01)

(58) Field of Classification Search
CPC ........ G01N 27/00; G01N 27/02; G01N 27/04; G01N 27/12; G01N 27/22; G01N 27/221;
(Continued)

(56) References Cited

U.S. PATENT DOCUMENTS 11,187,653 B2 * 11/2021 Wan .................... G01J 3/42

FOREIGN PATENT DOCUMENTS

CN    203259695 U  * 10/2013
CN    205484193 U    8/2016
(Continued)

*Primary Examiner* — Hoai-An D. Nguyen
(74) *Attorney, Agent, or Firm* — NKL LAW; Jae Youn Kim (57) ABSTRACT

Provided according to one embodiment is a device for sensing a gas, comprising: a lamp for outputting ultraviolet light; a first PCB including a hole for inserting the lamp; a second PCB disposed perpendicular to the first PCB and including a lamp power terminal and a lamp ground terminal used to supply power to the lamp; a third PCB disposed parallel to the first PCB, disposed perpendicular to the second PCB, and including a power reception terminal for receiving power from the outside; a first ring-shaped electrode attached to the lamp power terminal and fixing the lamp; and a second ring-shaped electrode attached to the lamp ground terminal, fixing the lamp, and disposed parallel to the first electrode.

7 Claims, 9 Drawing Sheets

(58) Field of Classification Search
CPC .. G01N 27/22262; G01N 21/00; G01N 21/17; G01N 21/25; G01N 21/31; G01N 33/00; G01N 33/0004; G01N 33/0009; G01N 33/0027; G01N 33/0036
USPC .................................................. 324/459, 464
See application file for complete search history.

(56) References Cited

FOREIGN PATENT DOCUMENTS

| | | | |
|---|---|---|---|
| CN | 210155000 U | * | 3/2020 |
| CN | 210774169 U | * | 6/2020 |
| CN | 113009064 A | * | 6/2021 |
| JP | 2003-098153 A | | 4/2003 |
| JP | 5923284 B2 | | 5/2016 |
| KR | 10-2004-0036470 A | | 4/2004 |
| KR | 10-2017-0022751 A | | 3/2017 |

* cited by examiner

VOC DETECTION PID GAS SENSOR DEVICE

TECHNICAL FIELD

The present invention relates to a device for sensing gas. More specifically, the present invention relates to a device capable of precisely sensing ionized gas based on ring-shaped electrodes which fix a lamp.

BACKGROUND ART

Volatile organic compounds (VOCs) are widely used not only in industrial manufacturing facilities but also in living spaces, and thus are exposed to the surrounding environment. Since the dangers of such organic compounds are known as factors causing infant atopic skin disease, odor and cancer, etc., the government has implemented various legal regulations such as "Indoor Air Quality Management Act for Multi-use Facilities," "Indoor Air Quality Recommendation Standards for New Apartment Houses," etc.

As sensor technologies for detecting organic compounds, gas-reactive gas sensors using electrochemicals and metal oxides, and optical gas sensors using light are provided.

Gas-reactive gas sensors have disadvantages such as short lifespan, and problems such that sensor performance varies according to environmental changes such as change in water content and temperature. Accordingly, many researches are in progress to improve the conventional problems and ensure sensor performance.

SUMMARY OF INVENTION

Technical Task

An embodiment of the present invention may provide a device capable of solving the above-described problems of prior art by providing a device for sensing gas, and more specifically, a device capable of precisely sensing ionized gas based on ring-shaped electrodes which fix a lamp.

In addition, an embodiment of the present invention may provide a device capable of improving the output efficiency of a lamp outputting extreme ultraviolet energy and precisely detecting various types of volatile organic compound gases.

The object of the present invention is not limited to the objects mentioned above, and other objects not mentioned can be clearly understood from the following description.

Means for Solving Technical Task

The device for sensing gas according to an aspect of the present invention may comprise: a lamp for outputting ultraviolet light; a first PCB including a hole for inserting the lamp; a second PCB disposed perpendicular to the first PCB and including a lamp power terminal and a lamp ground terminal used to supply power to the lamp; a third PCB disposed parallel to the first PCB, disposed perpendicular to the second PCB, and including a power reception terminal for receiving power from the outside; a first ring-shaped electrode attached to the lamp power terminal and fixing the lamp; and a second ring-shaped electrode attached to the lamp ground terminal, fixing the lamp, and disposed parallel to the first electrode.

In addition, the device may further comprise a plurality of sensing electrodes positioned in a direction in which the lamp outputs ultraviolet light, and passing a current having a size determined according to the amount of ionized gas.

In addition, the device may further comprise an insulator positioned between the plurality of sensing electrodes.

In addition, a first time point at which a current is applied to the plurality of sensing electrodes is later than a second time point at which current is applied to the lamp power terminal, and the magnitude of the current flowing through the plurality of sensing electrodes at the first time point may be 90% or above the magnitude of the saturation current, which is the magnitude of the current flowing through the plurality of sensing electrodes after a sufficient amount of time has passed.

In addition, the device may further comprise a third ring-shaped electrode attached to the lamp power terminal, fixing the lamp, and disposed parallel to the first electrode and the second electrode.

In addition, the voltage applied to the first electrode and the voltage applied to the third electrode may be determined to be the same or different based on a user input.

In addition, the lamp may comprise: a window for outputting the ultraviolet light; and a tube attached to a lower end of the window, and the tube may comprise a first shape attached to the window, which is part of a cone whose diameter gets smaller toward the lower side, a second shape positioned at a lower end of the first shape, which is a cylinder shape with the same diameter, a third shape positioned at a lower end of the second shape, which is part of a cone whose diameter gets smaller toward the lower side, and a fourth shape positioned at a lower end of the third shape, which is a cylinder shape with the same diameter.

Effect of Invention

According to an embodiment of the present invention, a device capable of precisely sensing ionized gas may be provided.

In addition, the output efficiency of a lamp outputting extreme ultraviolet energy may be improved and various types of volatile organic compound gases may be precisely detected.

In addition, the lifespan may be improved, and the problem that the sensor performance varies according to environmental changes such as change in water content and temperature may be improved.

The effects of the present invention are not limited to the above-mentioned effects, and it should be understood that the effects of the present invention include all effects that could be inferred from the configuration of the invention described in the detailed description of the invention or the appended claims.

DETAILED MEANS FOR CARRYING OUT THE INVENTION

Hereinafter, the present invention will be explained with reference to the accompanying drawings. The present invention, however, may be modified in various different ways, and should not be construed as limited to the embodiments set forth herein. Also, in order to clearly explain the present invention, portions that are not related to the present invention are omitted, and like reference numerals are used to refer to like elements throughout.

Throughout the specification, it will be understood that when a portion is referred to as being "connected" to another portion, it can be "directly connected to" the other portion, or "indirectly connected to" the other portion having intervening portions present. Also, when a component "includes" an element, unless there is another opposite description thereto, it should be understood that the component does not exclude another element but may further include another element.

Throughout the specification, "device" or "gas sensing device" may be understood as a concept including a VOC detection PID gas sensor device. A photoionization detector (PID) may be used in a gas sensing device.

Hereinafter, the embodiments of the present invention will be described in detail with reference to the accompanying drawings.

Figure 1:
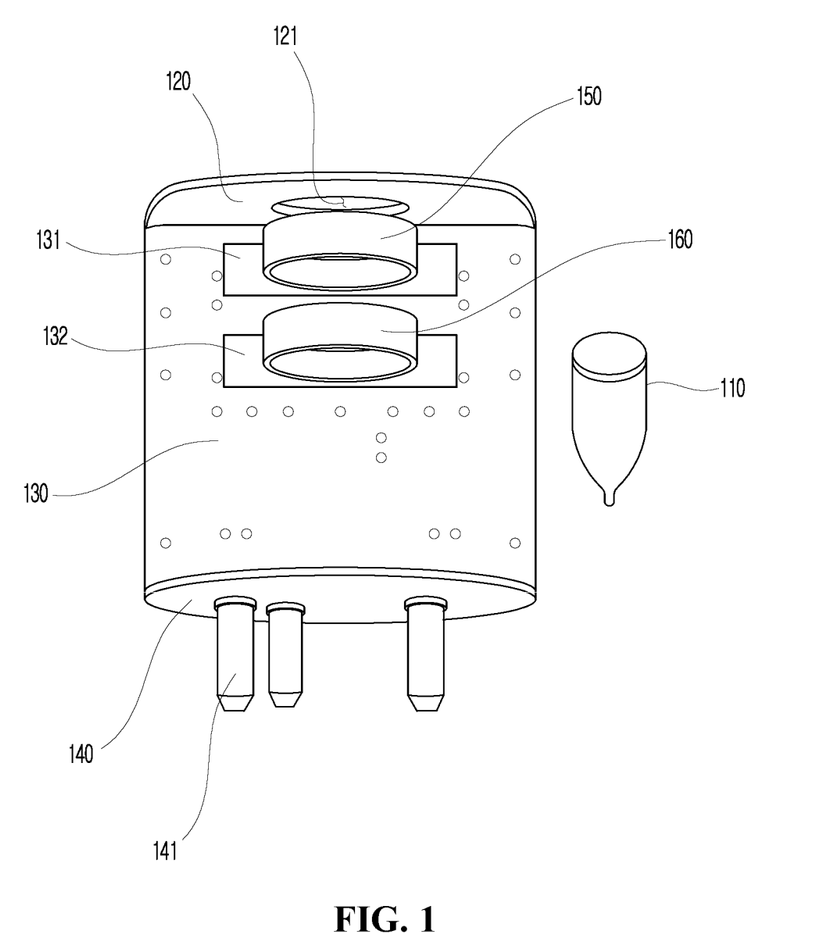
FIG. 1 is a perspective view illustrating an example of the configuration of a gas sensing device according to an embodiment.
Figure 2:
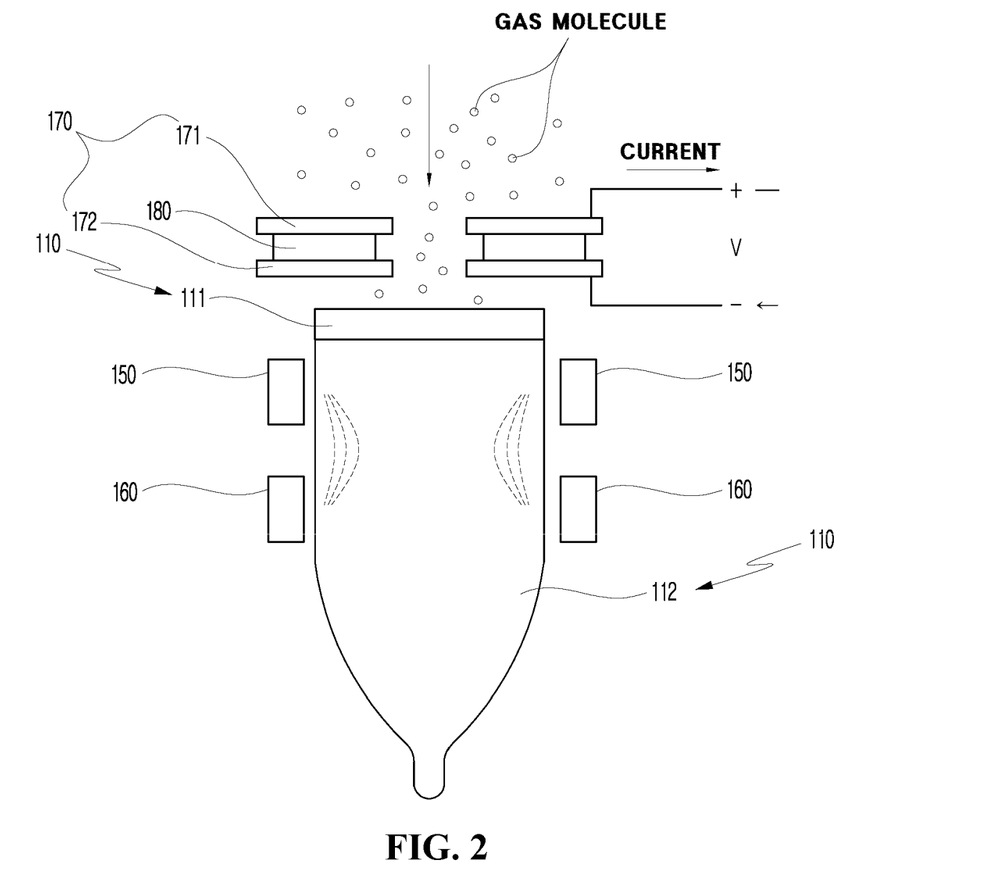
FIG. 2 is a cross-sectional view illustrating part of the configuration of a gas sensing device in order to explain the operation of the gas sensing device illustrated in FIG. 1 sensing gas.

FIG. 1 is a perspective view illustrating an example of the configuration of a gas sensing device 100 according to an embodiment. FIG. 2 is a cross-sectional view illustrating part of the configuration of a gas sensing device 100 in order to explain the operation of the gas sensing device 100 illustrated in FIG. 1 sensing gas.

With reference to FIGS. 1 and 2, the gas sensing device 100 may sense gas, and according to an embodiment, the gas sensing device 100 may be implemented as a photoionization detector capable of detecting the concentration of a volatile organic compound-based gas substance (e.g., isobutylene) in a predetermined range of concentration (e.g., 0 to 2000 pm).

The gas sensing device 100 according to an embodiment may comprise a lamp 110, a first PCB 120, a second PCB 130, a third PCB 140, a first electrode 150, a second electrode 160, a plurality of sensing electrodes 170 and an insulator 180.

The lamp 110 according to an embodiment may output ultraviolet light, and for example, may be implemented as a halogen lamp using metal halide gas which generates extreme ultraviolet light presenting electromagnet waves of a predetermined extreme ultraviolet wavelength (e.g., 10 nm to 124 nm).

The lamp 110 according to an embodiment may comprise a window 111 and a tube 112.

The window 111 according to an embodiment may output ultraviolet light, and for example, may transmit the extreme ultraviolet light emitted from the tube 112 attached to a lower end toward the upper part.

According to an embodiment, the window 111 may comprise a metal halogen capable of passing through a short wavelength region whose wavelength is smaller than or equal to a predetermined wavelength, and for example, may be implemented as an optical thin film formed through deposition of magnesium fluoride ($MgF_2$), so as to transmit the extreme ultraviolet light generated in the tube 112 to the outside of the lamp 110. According to an embodiment, the window 111 may comprise a transmissive material such as crystal, gas, or a thin metal film made of magnesium fluoride ($MgF_2$), calcium fluoride ($CaF_2$), or barium fluoride ($BaF_2$).

The tube 112 according to an embodiment may be attached to a lower end of the window 111, and for example, one surface attached to a lower end of the window 111 may comprise a transmissive material configured to pass through a short wavelength region whose wavelength is smaller than or equal to a predetermined wavelength, and the housing of the surfaces other than the one surface may comprise a non-transmissive material configured not to pass through a short wavelength region whose wavelength is smaller than or equal to a predetermined wavelength.

When a voltage is applied, the tube 112 according to an embodiment may discharge the discharge gas contained therein to generate ultraviolet light. For example, when a voltage is applied from a first electrode 150 and a second electrode 160, the tube 112 may discharge metal halide gas (e.g., calcium fluoride ($CaF_2$), hydrogen gas or inert gas, etc. contained in a vacuum-formed housing to generate extreme ultraviolet light, and guide the extreme ultraviolet light to move to a lower end of the window 111.

The lamp 110 according to an embodiment may be implemented to be mounted on the gas sensing device 100, and for example, may be inserted into an empty space formed inside the first electrode 150 and the second electrode 160 by a user, and coupled to the gas sensing device 100.

The first PCB 120 according to an embodiment may comprise a hole 121 for inserting the lamp 110. Here, the hole 121 may represent an empty space formed in a part of the first PCB 120, and according to an embodiment, the hole 121 may provide a space for gas in the air to move or gas to be ionized.

When a plurality of sensing electrodes 170 are attached to an upper end of the first PCB 120 according to an embodiment, the first PCB 120 may sense whether a current greater than or equal to a predetermined magnitude flows through the plurality of sensing electrodes 170. For example, a plurality of sensing electrodes 170 may be disposed on an upper end of a part including a hole 121 in the first PCB 120, and the first PCB 120 may be electrically connected to each of the plurality of sensing electrodes 170 to apply power (e.g., DC bias voltage), and may sense whether a current flows through the plurality of sensing electrodes 170 and the amount of current flowing according to the gas ionized by extreme ultraviolet light.

The first PCB 120 according to an embodiment may comprise at least one of a power circuit for providing power (e.g., DC bias voltage) to the plurality of sensing electrodes 170, a band-pass filter (e.g., HPF, LPF, etc.) for filtering a signal corresponding to the magnitude of the current flowing through the plurality of sensing electrodes 170 to a predetermined frequency range, an amplification circuit for amplifying the filtered signal to determine whether the signal exceeds a predetermined threshold, and a determining circuit for determining whether to detect a target gas (e.g., volatile organic compound) according to the amplified signal.

The second PCB 130 according to an embodiment may be disposed perpendicular to the first PCB 120, and for example, may be disposed between a lower end of the first PCB 120 and an upper end of the third PCB 140, and disposed perpendicular to the hole 121, so as to be disposed parallel to the lamp 110 when the lamp 110 is positioned inside the first electrode 150 and the second electrode 160.

The second PCB 130 according to an embodiment may comprise a lamp power terminal 131 and a lamp ground terminal 132 used to supply power to the lamp 110.

The lamp power terminal 131 according to an embodiment may be electrically connected to the first electrode 150 to supply power to the first electrode 150, and for example, when a first electrode 150 is attached thereto, a power voltage of a predetermined magnitude may be applied to the first electrode 150.

The lamp ground terminal 132 according to an embodiment may be electrically connected to the second electrode 160 to supply power to the second electrode 160, and for example, when a second electrode 160 is attached thereto, a ground voltage of a predetermined magnitude may be applied to the first electrode 150.

The second PCB 130 according to an embodiment may be electrically connected to the first PCB 120, and may output a gas detection result based on the signal received from the first PCB 120. According to an embodiment, the second PCB 130 may comprise at least one of a band-pass filter (e.g., HPF, LPF, etc.), an amplification circuit, and a determining circuit, and when it is determined that gas (e.g., volatile organic compound) is detected based on the signal received from the first PCB 120, the second PCB may comprise an output circuit (e.g., LED module, sound module, etc.) for outputting the gas detection result according to a predetermined method (e.g., LED lighting, warning sound output, etc.).

The second PCB 130 according to an embodiment may be electrically connected to the third PCB 140, may receive power from the third PCB 140, and may comprise a power control circuit for providing power and ground to the lamp power terminal 131 and lamp ground terminal 132 using the supplied power.

The third PCB 140 according to an embodiment may be disposed parallel to the first PCB 120 and may be disposed perpendicular to the second PCB 130. According to an embodiment, the third PCB 140 may be disposed at one end of the second PCB 130, and disposed in a direction parallel to the hole 121, so as to be disposed perpendicular to the longitudinal direction of the lamp 110 when the lamp 110 is positioned inside the first electrode 150 and the second electrode 160.

The third PCB 140 according to an embodiment may comprise a power receiving terminal 141 for receiving power from the outside, and for example, may comprise a first power receiving terminal for receiving a power voltage (e.g., $V_{CC}$ 5V) and a second power receiving terminal for ground (e.g., GND 0V), and may further comprise an output transmission terminal for transmitting output voltage (e.g., $V_{OUT}$). According to an embodiment, the third PCB 140 may further comprise a battery module for storing the received power.

The first electrode 150 according to an embodiment may be attached to the lamp power terminal 131, and for example, may be fixed by being coupled to a coupling member formed on the lamp power terminal 131 through a coupling member formed at one end.

The first electrode 150 according to an embodiment may have a ring shape for fixing the lamp 110. For example, the ring-shaped inner radius may be formed to be smaller than or equal to a predetermined first value as compared to the outer radius of the housing formed in the lamp 110, thereby fixing an upper part of the lamp 110 so that the lamp 110 does not move and apply power voltage supplied from the lamp power terminal 131 to the lamp 110.

The second electrode 160 according to an embodiment may be attached to the lamp ground terminal 132, and for example, may be fixed by being coupled to a coupling member formed on the lamp ground terminal 132 through a coupling member formed at one end.

The second electrode 160 according to an embodiment may have a ring shape for fixing the lamp 110, which is disposed parallel to the first electrode 150. For example, the second electrode 160 may have the ring-shaped inner radius formed to be smaller than or equal to a predetermined second value as compared to the outer radius of the housing formed in the lamp 110, thereby fixing a lower part of the lamp 110 so that the lamp 110 does not move and apply ground voltage supplied from the lamp ground terminal 132 to the lamp 110.

According to an embodiment, the first value and the second value may be the same or different, and for example, the second value may be smaller than the first value. Details regarding this embodiment will be described later with reference to FIGS. 4 and 5.

The plurality of sensing electrodes 170 according to an embodiment may be positioned in a direction in which the lamp 110 outputs ultraviolet light, and may transmit a current having a magnitude determined according to the amount of ionized gas. For example, the plurality of sensing electrodes 170 may be disposed on an upper part of the hole 121 through which the extreme ultraviolet light generated from the lamp 110 passes, so as to allow the current to flow according to the potential formed by positive charges and electrons, which are gas ionized by extreme ultraviolet light.

The plurality of sensing electrodes 170 according to an embodiment may be used to detect volatile organic compound gas ionized by the extreme ultraviolet light output from the lamp 110. For example, each of the plurality of sensing electrodes 170 may comprise a connection terminal (refer to reference numerals 710 to 730) which may be electrically connected to the first PCB 120, and receive power from a first PCB 120 through the connection terminal and transmit the current passing through by ionized gas to the first PCB 120, thereby supporting the sensing of the current magnitude and the generation of gas detection result by a first PCB 120 or a second PCB.

According to an embodiment, the plurality of sensing electrodes 170 may comprise two sensing electrodes. For example, the plurality of sensing electrodes 170 may comprise a first sensing electrode 171 formed on an upper part of the insulator 180 and a second sensing electrode 172 formed on a lower part of the insulator 180. When a neutral volatile organic compound gas is ionized by the extreme ultraviolet light output from the lamp 110 and separated into positive charges and electrons, a power voltage is applied so that the electrons move to the first sensing electrode 171 operating as an anode, and a ground voltage is applied so that the positive charges move to the second sensing electrode 172 operating as a cathode. Accordingly, when the potential between the first sensing electrode 171 and the second sensing electrode 172 is formed at a predetermined value or above, a current corresponding thereto may be transmitted and provided to the first PCB 120.

According to another embodiment, the plurality of sensing electrodes 170 may comprise three or more sensing electrodes. This will be described later with reference to FIGS. 6 to 8.

The insulator 180 according to an embodiment may be positioned between the plurality of sensing electrodes 170, for example, between the first sensing electrode 171 in the upper part and the second sensing electrode 172 in the lower part to space the first sensing electrode 171 and the second sensing electrode 172. According to an embodiment, the insulator 180 may be implemented as a silicon compound (e.g., $SiO_2$), etc.

In addition, a person skilled in the art may understand that the gas sensing device 100 may further comprise other generally used components in addition to those illustrated in FIG. 1. For example, the gas sensing device 100 may further comprise a memory for storing data required for the overall operation of gas sensing and a processor for controlling the overall operation of gas sensing, and may further comprise a high voltage generator, a high voltage RF driver, a sensing electrode high voltage driving circuit and a micro sensor signal processing circuit, etc. Also, according to another embodiment, some of the components illustrated in FIG. 1 may be omitted.

With reference to FIG. 2, the lamp 110 according to an embodiment may be mounted and fixed to a ring-shaped first electrode 150 and second electrode 160. When a power voltage and a ground voltage are applied to the first electrode 150 and the second electrode 160, respectively, a metal halide gas such as calcium fluoride ($CaF_2$) contained in the tube 112 may be discharged to generate extreme ultraviolet light.

As described above, the first electrode 150 and the second electrode 160 may respectively come into contact with the surface from the outside of the lamp 110 or surround the periphery of the lamp 110 in a ring shape within a predetermined distance to supply power to the inside. For example, the first electrode 150 may apply a power voltage to the ring-shaped periphery from an upper surface of the lamp 110, and the second electrode 160 may apply a ground voltage to the ring-shaped periphery from a lower surface of the lamp 110.

Accordingly, the electric field formed inside the tube 112 may be formed in various directions and various magnitudes throughout the inside of the tube 112, rather than being formed by simply traversing the inside of the tube 112 in a straight line. Such structure of the present invention may greatly improve the discharge efficiency of the inside of the tube 112, and remarkably improve the efficiency of generating extreme ultraviolet light.

As described above, the lamp 110 according to an embodiment may output extreme ultraviolet light toward the hole 121 of the first PCB 120, and the extreme ultraviolet light output as above may collide with the molecules of volatile organic compound gas floating in the hole 121 or its surrounding and ionize the gas molecules. Since the ionization energy levels vary depending on the volatile organic compound gases, the volatile organic compound gases which can be sensed may be separated according to the energy level of the extreme ultraviolet light output by the lamp 110. For example, when the lamp 110 outputs an extreme ultraviolet light having an energy level of 9.8 eV, styrene having an ionization energy level of 8.4 eV, benzene having an ionization energy level of 9.24 eV, etc. may be sensed.

The plurality of sensing electrodes 170 according to an embodiment may be disposed on the first PCB 120, and when gas molecules of a neutral volatile organic compound are ionized by extreme ultraviolet light and generate a plurality of positive charges and electrons, the positive charges or electrons may be accumulated to operate as an anode or a cathode. Also, when a potential of a predetermined value or above is formed according to the accumulation of the positive charges or electrons, a current of a magnitude determined according to the amount of gas is transmitted as an electrical signal to the first PCB 120 through the connection terminal.

The first PCB 120 according to an embodiment may sense the magnitude of the current based on the electrical signal received from the plurality of sensing electrodes 170, and the second PCB 130 may determine the type of gas detected and the amount of gas detected by analyzing a signal corresponding to the magnitude of the current received from the first PCB 120 based on the energy level of the extreme ultraviolet light output by the lamp 110. Also, when the amount of gas detected corresponds to the type of a corresponding gas and is greater than a predetermined reference value, the first PCB 120 turns on the built-in LED module and outputs a warning sound to the built-in sound module to notify gas detection.

According to an embodiment, a first time point at which a current is applied to the plurality of sensing electrodes 170 is later than a second time point at which a current is applied to the lamp power terminal 131, and the magnitude of the current flowing through the plurality of sensing electrodes 170 at the first time point may be 90% or above the magnitude of the saturation current, which is the magnitude of the current flowing through the plurality of sensing electrodes 170 after a sufficient amount of time has passed. For example, time t90 may represent a time spent for the magnitude of a sensed current to reach 90% of the magnitude of the saturation current. By setting the first time point to be time t90 or thereafter, it is possible to reduce unnecessary power consumption, and prevent misunderstanding of numerical values by preventing incorrect numerical values from being displayed in advance.

Figure 3:
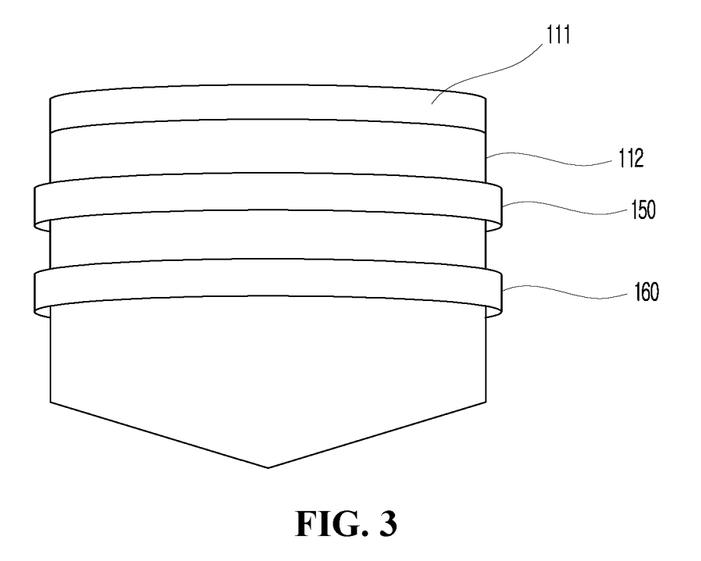
FIG. 3 is a view illustrating part of the configuration of a gas sensing device in order to explain various embodiments of the gas sensing device illustrated in FIG. 1.
Figure 4:
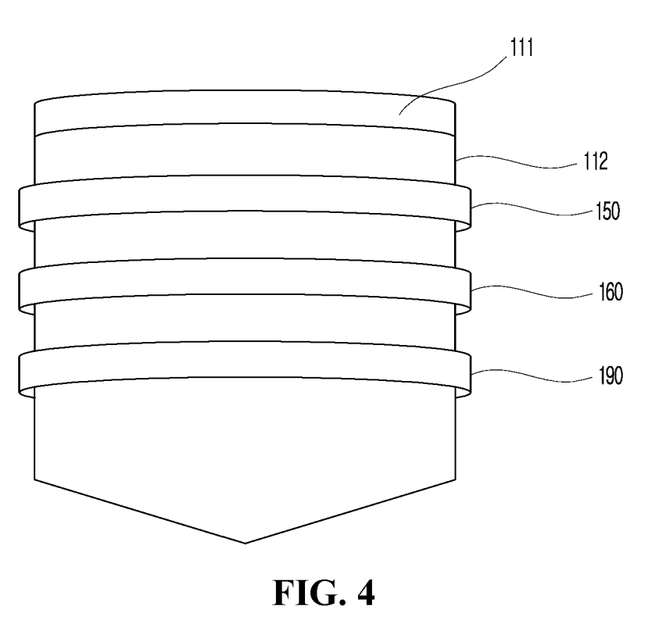
FIG. 4 is a view illustrating part of the configuration of a gas sensing device in order to explain various embodiments of the gas sensing device illustrated in FIG. 1.
Figure 5:
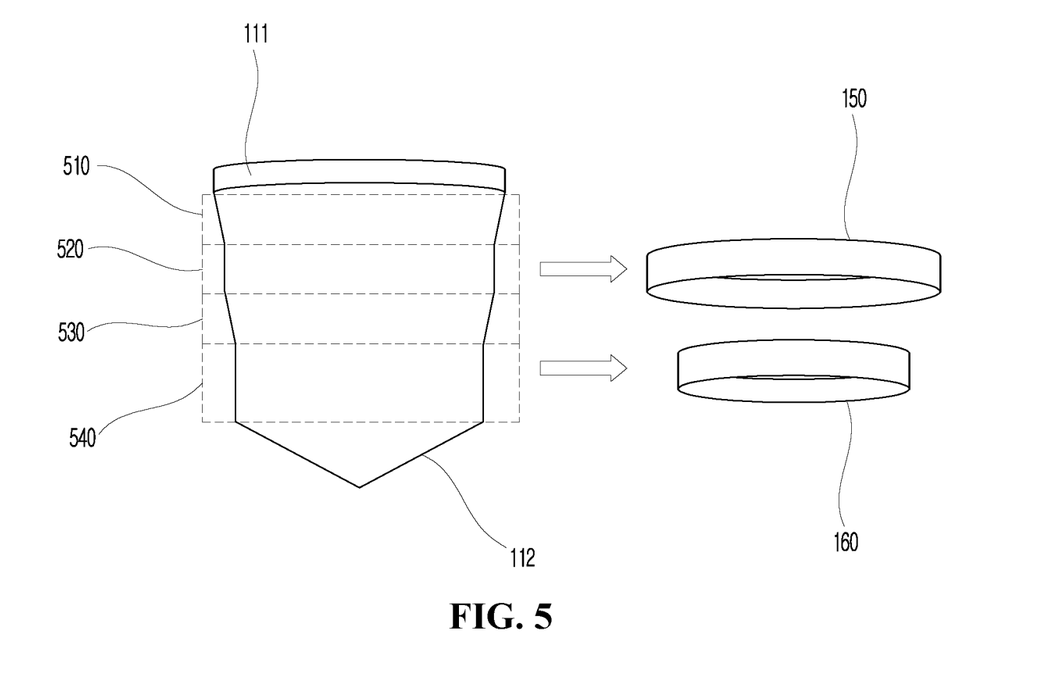
FIG. 5 is a view illustrating part of the configuration of a gas sensing device in order to explain various embodiments of the gas sensing device illustrated in FIG. 1.

FIGS. 3 to 5 are views illustrating parts of the configuration of a gas sensing device 100 in order to explain various embodiments of the gas sensing device 100 illustrated in FIG. 1 sensing gas.

With reference to FIG. 3, the gas sensing device 100 according to an embodiment may comprise a ring-shaped first electrode 150 and a second electrode 160 for fixing the lamp 110 as described above. The first electrode 150 and the second electrode 160 may fix the tube 112 and provide power to the tube 112 when the lamp 110 is disposed in an empty space formed inside the first electrode 150 and the second electrode 160, respectively.

With reference to FIG. 4, the gas sensing device 100 according to an embodiment may further comprise a ring-shaped third electrode 190 which is attached to the lamp power terminal 131, fixes the lamp 110, and is disposed parallel to the first electrode 150 and the second electrode 160. For example, the lamp power terminal 131 may comprise a first lamp power terminal and a second lamp power terminal. The gas sensing device 100 may apply a power voltage (e.g., 1.8 V) to the first electrode 150 through the first lamp power terminal formed at one end of the second PCB 130, apply a ground voltage (e.g., 0 V) to the second electrode 160 through the lamp ground terminal 132 formed at one end of the second PCB 130 and disposed at a lower part of the first lamp power terminal, and apply a power voltage (e.g., 1.8 V) to the third electrode 190 through the second lamp power terminal formed at one end of the second PCB 130 and disposed at a lower part of the lamp ground terminal 132.

Accordingly, according to the power applied from the first electrode 150, the second electrode 160 and the third electrode 190 which respectively surround the surface of the upper part, middle part and lower part in a ring shape, the range of influence of the electric field may be extended from the middle part connected to the second electrode 160 to the upper part and lower part, respectively, to be extended throughout the entire interior of the tube 112, thereby further improving the ultraviolet light output efficiency.

According to an embodiment, the voltage applied to the first electrode 150 and the voltage applied to the third electrode 190 may be determined to be the same or different based on a user input. According to an embodiment, the voltage (e.g., 1.8 V) applied to the third electrode 190 may be determined to be greater than the voltage (e.g., 1.5 V) applied to the first electrode 150.

According to an embodiment, the voltage applied to the first electrode 150 may be determined to be in proportion to a first distance between the window 111 and the first electrode 150 and to be in inverse proportion to a second distance between the window 111 and the third electrode 190. For example, the voltage applied to the first electrode 150 and the third electrode 190 may be determined according to the following equation 1, respectively. Accordingly, it is possible to control discharge to occur more strongly in an upper part of the tube 112 which is positioned relatively closer to the window 111, and in a lower part of the tube 112 which is positioned relatively farther from the window 111.

$$V_1 = V_{CC} * (L_1/L_2)$$ [Equation 1]
$$V_2 = V_{CC}$$

(here, $V_1$ and $V_2$ represent the magnitude of voltage applied to first electrode 150 and third electrode 190, respectively, $V_{CC}$ represents the magnitude of a predetermined DC power voltage, $L_1$ represents first distance between window 111 and first electrode 150, and $L_2$ represents second distance between window 111 and third electrode 190)

With reference to FIG. 5, the tube 112 according to an embodiment may comprise a first shape 510, a second shape 520, a third shape 530, and a fourth shape 540.

According to an embodiment, the first shape 510 may be a shape attached to the window 111, which is part of a cone whose diameter gets smaller toward the lower side. For example, it may be implemented as a shape slanted in a straight line or a shape slanted in a curve whose diameter gets smaller.

According to an embodiment, the second shape 520 may be a shape positioned at a lower end of the first shape 510, which is a cylinder shape with the same diameter. For example, it may be implemented as a shape with the same diameter, continuing from a lower end of the first shape 510 which is in a form slanted in a straight line whose diameter gets smaller.

According to an embodiment, the third shape 530 may be a shape positioned at a lower end of the second shape 520, which is part of a cone whose diameter gets smaller toward the lower side. For example, it may be implemented as a shape slanted in a straight line or a shape slanted in a curve whose diameter gets smaller, continuing from a lower end of the second shape 520 which is a shape with the same diameter.

According to an embodiment, the fourth shape 540 may be a shape positioned at a lower end of the third shape 530, which is a cylinder shape with the same diameter. For example, it may be implemented as a shape with the same diameter, continuing from a lower end of the third shape 530 which is in a form slanted in a straight line whose diameter gets smaller. Accordingly, the fourth shape 540 may have a diameter smaller than the third shape 530.

According to an embodiment, the inner diameter of the first electrode 150 may be the same as or greater than the outer diameter of the second shape 520 by less than a predetermined value, and the inner diameter of the second electrode 160 may be the same as or greater than the outer diameter of the fourth shape 540 by less than a predetermined value. Accordingly, the inner diameter of the first electrode 150 may be larger than the inner diameter of the second electrode 160.

Accordingly, in the above described embodiments, when the lamp 110 is mounted inside the ring-shaped first electrode 150 and second electrode 160, the fourth shape 540 in a cylindrical shape with a first diameter may be inserted while being engaged with the inside of the second electrode 160, and the third shape 530 which is part of a cone whose diameter gets smaller toward the lower side may assist the coupling between the fourth shape 540 and the second electrode 160 to be better fixed. In addition, the second shape 520 in a cylindrical shape with a second diameter larger than the first diameter may be inserted while being engaged with the inside of the first electrode 150, and the first shape 510 which is part of a cone whose diameter gets smaller toward the lower side may assist the coupling between the second shape 520 and the first electrode 150 to be better fixed.

Figure 6:
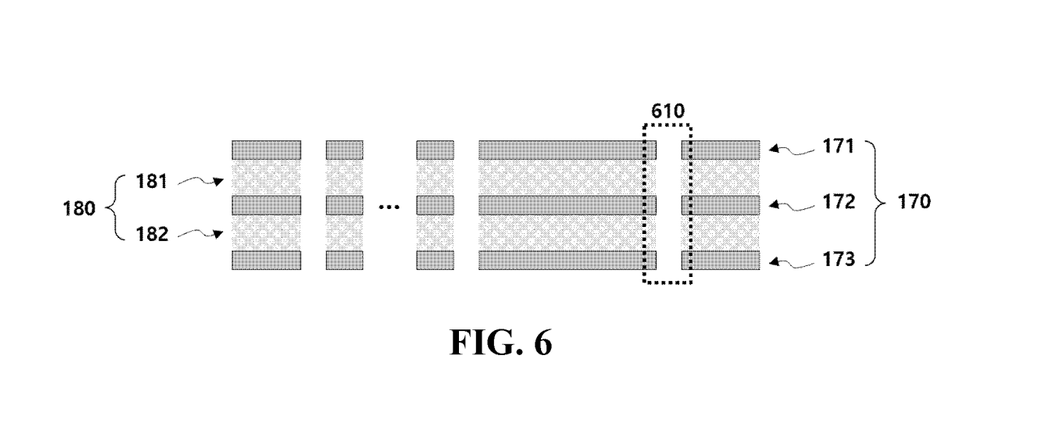
FIG. 6 is a cross-sectional view illustrating a structure of a cross-section of a plurality of sensing electrodes 170 included in the gas sensing device according to an embodiment.
Figure 7:
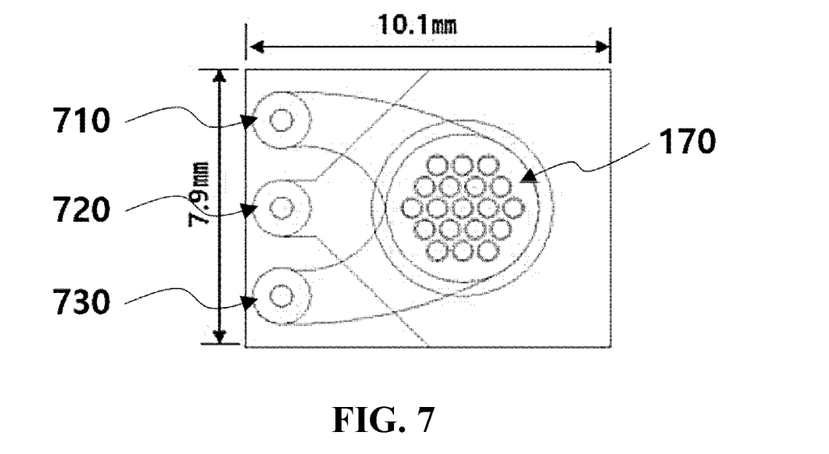
FIG. 7 is a cross-sectional view illustrating the exterior of the plurality of sensing electrodes illustrated in FIG. 6 seen from above.
Figure 8:
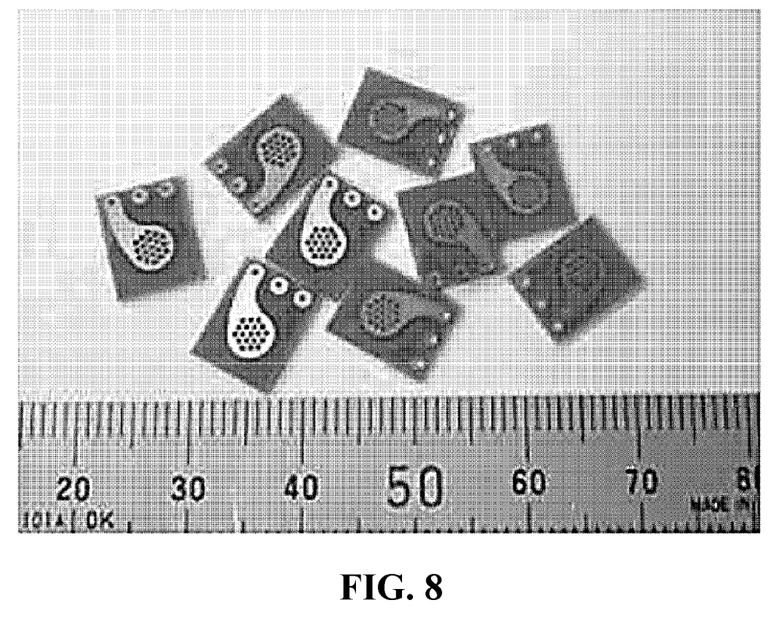
FIG. 8 is a view illustrating an embodiment implementing the plurality of sensing electrodes illustrated in FIG. 6 as an actual product.

FIG. 6 is a cross-sectional view illustrating a structure of a cross-section of a plurality of sensing electrodes 170 included in the gas sensing device 100 according to an embodiment. FIG. 7 is a cross-sectional view illustrating the exterior of the plurality of sensing electrodes 170 illustrated in FIG. 6 seen from above. FIG. 8 is a view illustrating an embodiment implementing the plurality of sensing electrodes 170 illustrated in FIG. 6 as an actual product.

With reference to FIG. 6, the plurality of sensing electrodes 170 may comprise three or more sensing electrode layers, and the insulator 180 may comprise two or more insulating layers.

Specifically, the plurality of sensing electrodes 170 may comprise a first sensing electrode 171, a second sensing electrode 172, and a third sensing electrode 173, and the insulator 180 may comprise a first insulator 181 and a second insulator 182. In addition, the first insulator 181 may be formed in a lower part of the first sensing electrode 171, the second sensing electrode 172 may be formed in a lower part of the first insulator 181, the second insulator 182 may be formed in a lower part of the second sensing electrode 172, and the third sensing electrode 173 may be formed in a lower part of the second insulator 182.

According to an embodiment, the first sensing electrode 171 and the third sensing electrode 173 may be implemented as a printed circuit substrate of a metal composite comprising at least one of gold (Au) and copper (Cu), and the second sensing electrode 172 may be implemented as a printed circuit substrate comprising copper.

With reference to FIGS. 6 and 7, the plurality of sensing electrodes 170 and the insulator 180 according to an embodiment may comprise a plurality of holes (refer to reference numeral 610), and through the plurality of holes (refer to reference numeral 610), the sensitivity may be improved to sense even gas of a lower concentration by increasing the surface area which may be in contact with the gas molecules floating in the air.

With reference to FIG. 7, each of the plurality of sensing electrodes 170 may be electrically connected to the first PCB 120 through a connection terminal. For example, a first sensing electrode 171, a second sensing electrode 172 and a third sensing electrode 173 may be attached to one or more of a first connection terminal (refer to reference numeral 710), a second connection terminal (refer to reference numeral 720), and a third connection terminal (refer to reference numeral 730) to be fixed to an upper part of the first PCB 120, and may be connected to the first PCB 120 to transmit or receive electrical signals such as receive DC bias voltage from the first PCB 120 or transmit a sensed current.

With reference to FIGS. 6 to 8, the plurality of sensing electrodes 170 may be implemented to comprise a plurality of holes (refer to reference numeral 610) so as to increase the surface area for gas sensing, and as illustrated in FIG. 8, may be implemented as a small electrode of about 5-10 mm.

Figure 9:
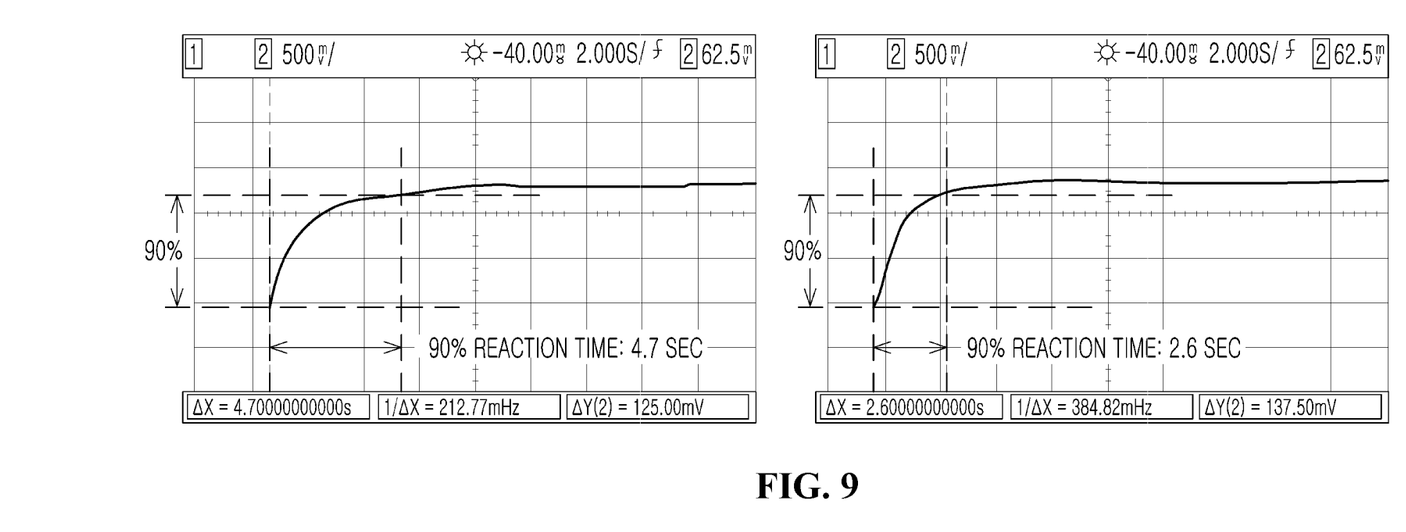
FIG. 9 is an exemplary view for explaining the operation of the gas sensing device illustrated in FIG. 1 sensing gas.

FIG. 9 is an exemplary view for explaining the operation of the gas sensing device illustrated in FIG. 1 sensing gas.

With reference to FIG. 9, the gas sensing device 100 may output extreme ultraviolet light for detecting isobutylene, sense the magnitude of current passing through the plurality of sensing electrodes 170, and detect isobutylene and determine the detected concentration (e.g., 0 to 2652 ppm) according to whether the magnitude of the current sensed is greater than or equal to a predetermined value.

When a current greater than or equal to a predetermined value is sensed, the gas sensing device 100 according to an embodiment may generate a signal indicating that gas is detected. For example, a voltage (or current) output according to the current sensed may vary from a low value (e.g., 0 V) to a high value (e.g., 1 V). Also, according to experimental results of an embodiment implementing the present invention illustrated in FIG. 9 as an actual product, it may be confirmed that time t90 which represents a time spent for the voltage (or current) output to reach 90% of the magnitude of the saturation voltage is measured to be between about 2.6 sec and 4.7 sec. In other words, it may be confirmed that a fast response time of about 3 to 5 sec is achieved until actual detection result is output after gas is discharged.

Figure 10:
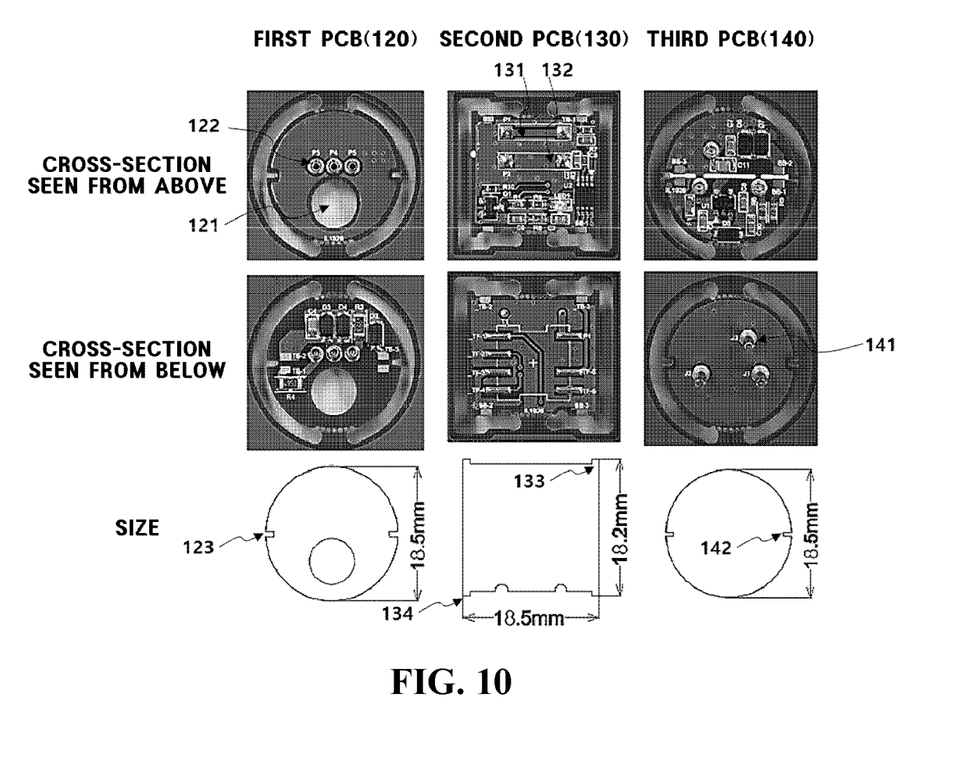
FIG. 10 is a view illustrating an embodiment implementing first to third PCBs included in the gas sensing device illustrated in FIG. 1 as an actual product.

FIG. 10 is a view illustrating an embodiment implementing first to third PCBs (120 to 140) included in the gas sensing device 100 illustrated in FIG. 1 as an actual product.

With reference to FIG. 10, the first PCB 120 comprises a hole 121, and thus when the plurality of sensing electrodes 170 are disposed on an upper part, the first PCB 120 allows the plurality of sensing electrodes 170 to be exposed to the ultraviolet light output from the lamp 110 so as to immediately react to the ionized gas, and the first PCB 120 may be connected to connection terminals (refer to reference numerals 710 to 730) in the plurality of sensing electrodes 170 through a plurality of terminals (refer to reference numeral 122).

In addition, the first PCB 120 may comprise a plurality of first grooves (refer to reference numeral 123) which may be coupled to an end of the second PCB 130, the second PCB 130 may comprise a plurality of second grooves (refer to reference numeral 133) which may be coupled to a plurality of first grooves (refer to reference numeral 123) and a plurality of third grooves (refer to reference numeral 134) which may be coupled to an end of the third PCB 140, and the third PCB 140 may comprise a plurality of fourth grooves (refer to reference numeral 142) which may be coupled to a plurality of third grooves (refer to reference numeral 134).

The foregoing description of the present invention has been presented for illustrative purposes, and it is apparent to a person having ordinary skill in the art that the present invention can be easily modified into other detailed forms without changing the technical idea or essential features of the present invention. Therefore, it should be understood that the forgoing embodiments are by way of example only, and are not intended to limit the present disclosure. For example, each component which has been described as a unitary part can be implemented as distributed parts. Likewise, each component which has been described as distributed parts can also be implemented as a combined part.

The scope of the present invention is presented by the accompanying claims, and it should be understood that all changes or m modifications derived from the definitions and scopes of the claims and their equivalents fall within the scope of the present invention.

The present invention may provide a device for sensing gas, and the gas sensing device 100 may comprise a device for sensing gas.

The invention claimed is:

1. A device for sensing gas, comprising:
a lamp for outputting ultraviolet light;
a first PCB including a hole for inserting the lamp;
a second PCB disposed perpendicular to the first PCB and including a lamp power terminal and a lamp ground terminal used to supply power to the lamp;
a third PCB disposed parallel to the first PCB, disposed perpendicular to the second PCB, and including a power reception terminal for receiving power from the outside;
a first ring-shaped electrode attached to the lamp power terminal and fixing the lamp; and
a second ring-shaped electrode attached to the lamp ground terminal, fixing the lamp, and disposed parallel to the first electrode.

2. The device of claim 1, further comprising a plurality of sensing electrodes positioned in a direction in which the lamp outputs ultraviolet light, and passing a current having a size determined according to the amount of ionized gas.

3. The device of claim 2, further comprising an insulator positioned between the plurality of sensing electrodes.

4. The device of claim 2, wherein a first time point at which a current is applied to the plurality of sensing electrodes is later than a second time point at which current is applied to the lamp power terminal, and the magnitude of the current flowing through the plurality of sensing electrodes at the first time point is 90% or above the magnitude of the saturation current, which is the magnitude of the current flowing through the plurality of sensing electrodes after a sufficient amount of time has passed.

5. The device of claim 2, further comprising a third ring-shaped electrode attached to the lamp power terminal, fixing the lamp, and disposed parallel to the first electrode and the second electrode.

6. The device of claim 5, wherein the voltage applied to the first electrode and the voltage applied to the third electrode are determined to be the same or different based on a user input.

7. The device of claim 1, wherein
the lamp comprises a window for outputting the ultraviolet light; and
a tube attached to a lower end of the window, wherein
the tube comprises a first shape attached to the window, which is part of a cone whose diameter gets smaller toward the lower side,
a second shape positioned at a lower end of the first shape, which is a cylinder shape with the same diameter,
a third shape positioned at a lower end of the second shape, which is part of a cone whose diameter gets smaller toward the lower side, and
a fourth shape positioned at a lower end of the third shape, which is a cylinder shape with the same diameter.

\* \* \* \* \*